(12) United States Patent
Kohls et al.

(10) Patent No.: US 7,499,825 B2
(45) Date of Patent: *Mar. 3, 2009

(54) PRINTED DIGITAL PHYSIOLOGICAL DATA SYSTEM AND METHOD

(75) Inventors: Mark Robert Kohls, New Berlin, WI (US); Bonnie Briny LeSourd, Hobe Sound, FL (US)

(73) Assignee: General Electric Co., Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/611,125

(22) Filed: Dec. 14, 2006

(65) Prior Publication Data

US 2007/0168149 A1 Jul. 19, 2007

Related U.S. Application Data

(63) Continuation-in-part of application No. 10/716,285, filed on Nov. 18, 2003, now Pat. No. 7,184,921.

(51) Int. Cl.
*G01D 1/00* (2006.01)
(52) U.S. Cl. .................................................. 702/127
(58) Field of Classification Search ............... 702/57, 702/66, 67, 127; 600/372, 373, 377, 382, 600/300, 301
See application file for complete search history.

(56) References Cited

U.S. PATENT DOCUMENTS

| 4,901,090 | A | * | 2/1990 | Ozawa et al. ............... 347/214 |
| 6,185,012 | B1 | * | 2/2001 | Yun ........................... 358/494 |
| 6,459,264 | B1 | | 10/2002 | Fain et al. |
| 6,463,320 | B1 | * | 10/2002 | Xue et al. .................... 600/523 |
| 6,520,910 | B1 | | 2/2003 | Kohls |
| 6,704,602 | B2 | | 3/2004 | Berg et al. |
| 6,748,256 | B2 | | 6/2004 | Brodnick et al. |
| 7,184,921 | B2 | * | 2/2007 | Kohls ......................... 702/127 |
| 7,261,387 | B2 | * | 8/2007 | Nishikori et al. ............... 347/15 |
| 2003/0144699 | A1 | | 7/2003 | Freeman |
| 2003/0152227 | A1 | * | 8/2003 | Javidi ......................... 380/219 |
| 2004/0138557 | A1 | | 7/2004 | Le et al. |
| 2004/0186357 | A1 | | 9/2004 | Soderberg et al. |
| 2005/0027201 | A1 | * | 2/2005 | Badilini et al. ............... 600/509 |
| 2005/0107978 | A1 | * | 5/2005 | Kohls ......................... 702/127 |

FOREIGN PATENT DOCUMENTS

DE 101 50 364 A1 4/2002

OTHER PUBLICATIONS

Data Matrix (computer), Wikipedia, printed date Apr. 21, 2008.*

* cited by examiner

*Primary Examiner*—Michael P Nghiem

(57) ABSTRACT

Various methods related to encoding and retrieving physiological data, such as digital ECG data, via a set of binary data are provided. In one embodiment, the set of binary data may be generated from the physiological data and printed on a printout of the physiological data or some other suitable medium. In another embodiment, the set of binary data may be scanned or otherwise acquired, and decoded to reconstruct all or a portion of the original set of physiological data. Additional methods and articles of manufacture are also provided.

17 Claims, 5 Drawing Sheets

PRINTED DIGITAL PHYSIOLOGICAL DATA SYSTEM AND METHOD

CROSS-REFERENCE TO RELATED APPLICATION

This application is a continuation-in-part of U.S. patent application Ser. No. 10/716,285, now U.S. Pat. No. 7,184,921, which was filed on Nov. 18, 2003 and entitled "Printed Digital ECG System and Method."

BACKGROUND

In general, the inventive arrangements relate to medical monitoring, and more specifically, to storing data, such as waveforms and/or other physiological data representations, acquired during medical monitoring, diagnostic testing, and/or the like. In particular, the inventive arrangements relate to generating a set of high-resolution characters representative of a set of physiological data, and to reconstructing a set of physiological data from such a set of high-resolution characters.

Electrocardiograph ("ECG") systems measure cardiac electrical activity associated with muscular pumping activities of the heart. Often, the electrical activity is measured by placing contacts or leads on the body of a patient. Typically, the measured electrical activity may then be printed out as an ECG waveform or trace for review by a doctor and/or diagnostician and/or the like.

In hospitals and other healthcare facilities, added functionality and workflow integration may be provided by digital ECG systems that acquire and store the ECG data in a digital format. The digital ECG data may be stored on various magnetic or optical devices, may be transmitted to one or more display stations remote from the patient, and may be printed once or numerous times from the stored record. The digital ECG data, therefore, provides a degree of flexibility, security, and reproducibility that may not be easily obtained from non-digital ECG systems that produce only a paper record of the ECG waveform or trace.

Despite the benefits of digital ECG, certain vulnerabilities may be created when using the digital technology. For example, digital records may be accidentally deleted, corrupted, or destroyed. Similarly, the accessible nature of digital records may create security or privacy concerns in the absence of a suitable controlled-access implementation. Furthermore, paper savings, i.e., paperless ECG, may not be realized due to advantages of paper printouts, such as superior resolution, ease of side-by-side comparison, convenience, and so forth. As a result, even in healthcare facilities utilizing digital ECGs, the actual implementation may be a combination of digital acquisition and storage with analog printouts remaining the primary presentation of the ECG data to the medical care provider.

Furthermore, outside of a hospital setting, for example, use of digital ECG is not widespread, with paper ECG printouts remaining the primary or only record of a set of ECG data. For example, ECG data may be collected during physical exams or clinical testing, such as at doctors' offices, universities, clinics, and so forth, where the workflow or limited nature of the facility does not justify the use of a digital ECG system. As a result, the ECG data collected may never be converted into a digital format or entered into a database or other shared or archival system. Furthermore, the paper ECG printout may be lost, damaged, or destroyed, with no way to recover or replace the ECG data acquired at that point in time. The present may be directed to one or more of the problems set forth above.

SUMMARY

Certain aspects commensurate in scope with the originally claimed invention are set forth below. It should be understood that these aspects are presented merely to provide the reader with a brief summary of certain forms the inventive arrangements might take and that these aspects are not intended to limit the scope of the inventive arrangements. Indeed, the inventive arrangements may encompass a variety of aspects that may not be set forth below.

Various embodiments of the present inventive arrangements generally relate to a novel technique and apparatus for storing and retrieving physiological data, such as digital ECG waveforms. In some embodiments, the technique provides for the receipt of a set of physiological data, and the generation of a set of high-resolution symbols from the set of physiological data. In one embodiment, the high-resolution symbols comprise a binary encoding of at least some portion of the physiological data. The set of high-resolution symbols may be printed on a suitable medium, such as part of a printout of the set of physiological data. In addition, the technique provides for reconstructing all or part of the original set of physiological data from the set of high-resolution symbols. The reconstructed physiological data may be stored or printed for future reference. Additionally, a novel printed medium for use with such techniques is also provided, which may, in certain embodiments, include at least one page registration mark to facilitate scanning and transmitting high-resolution symbols.

Various refinements of the features noted above may exist in relation to various aspects of the inventive arrangements. Further features may also be incorporated in these various aspects as well. These refinements and additional features may exist individually or in any combination. For instance, various features discussed below in relation to one or more of the illustrated embodiments may be incorporated into any of the above-described aspects of the present inventive arrangements alone or in any combination. Again, the summary presented above is intended only to familiarize the reader with certain aspects and contexts of the inventive arrangements without limitation to the claimed subject matter.

BRIEF DESCRIPTION OF SEVERAL VIEWS OF THE DRAWINGS

The foregoing and other advantages and features of the inventive arrangements will become apparent upon reading the following detailed description and upon reference to the drawings, in which.

DETAILED DESCRIPTION OF VARIOUS PREFERRED EMBODIMENTS

One or more specific embodiments of the present inventive arrangements will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present technique may be used in conjunction with any application in which data is customarily printed and where digital storage or transfer techniques are unavailable or impractical. For example, different types of equipment used to measure various physiological parameters may generate paper reports or printouts of the measured physiological data, in which the physiological data set is represented as waveforms, traces, or arbitrary numbers. Examples of these types of systems include pulse oximeters, blood pressure monitors, defibrillators, electrocardiographs, and so forth. To the extent that the printout or report is the only record of the physiological events measured at that time, it may be difficult or impossible to provide the analog physiological data contained in the report to a centralized digital system, such as a database, for storage and retrieval. However, it may be desirable to have a digital record of the physiological data contained in the printout, particularly, where the physiological data forms part of a medical or clinical history, such as for doctor or hospital records, or for pharmaceutical testing.

Accordingly, the present technique provides a mechanism by which physiological or other data may be provided on a printout or other printed medium in a digitized format. The digitized format may be used to subsequently reconstruct the data or provide the data to a database or other digital system. To simplify explanation, the present technique will be discussed in the context of a digital electrocardiograph ("ECG") system. However, as one of ordinary skill in the art will appreciate, the present technique may be applied to other systems that customarily print an analog data set, such as monitoring systems for different physiological parameters and so forth.

Figure 1:
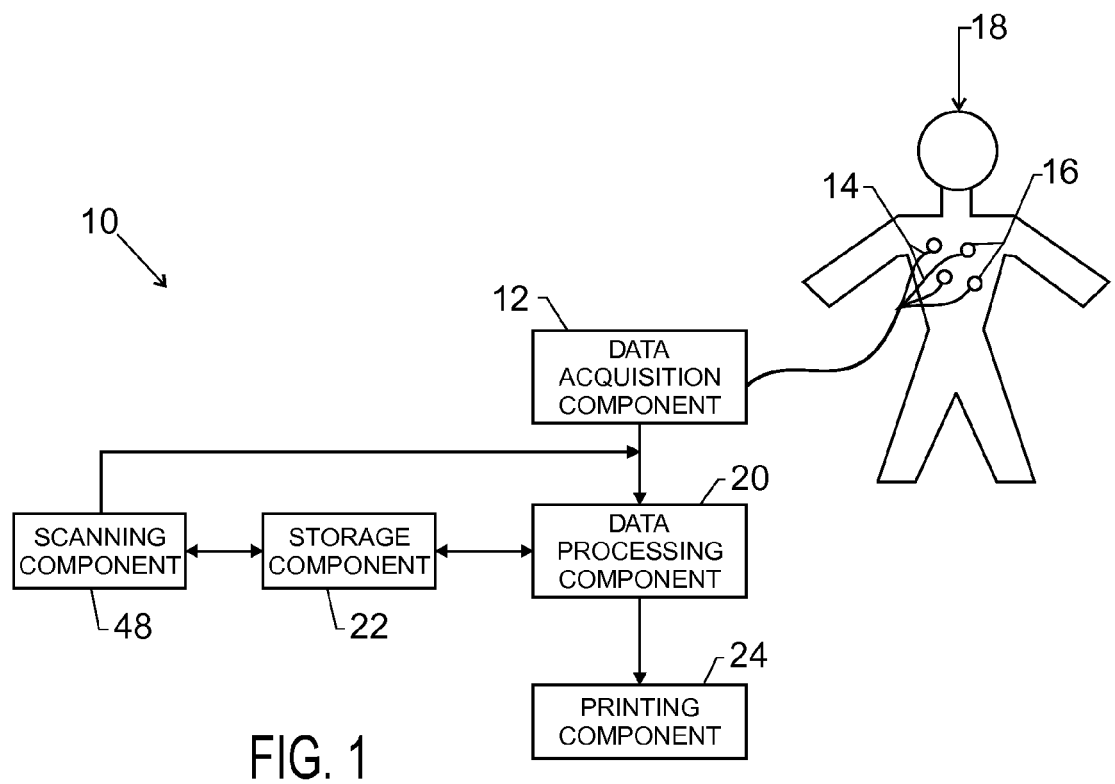
FIG. 1 is a diagrammatical view of an exemplary monitoring system in the form of an electrocardiograph for use in monitoring cardiac electrical activity, in accordance with one aspect of the present technique.

Turning now to the example of an ECG system, FIG. 1 depicts an exemplary ECG system 10 which may be used in conjunction with the present technique. The ECG system 10 may include a variety of components. For example, the ECG system 10 may include a data acquisition component 12 configured to receive electrical signals that convey the electrical activity of the heart, such as the polarization and depolarization events associated with cardiac contraction. The electrical signals may be conducted to the data acquisition component 12 via electrical leads 14 terminating in contact pads 16 which are positioned on the torso of the patient 18. While four leads 14 and contact pads 16 are depicted in FIG. 1 for simplicity, other numbers of leads 14 and contact pads 16 may be employed. In particular, twelve-lead ECG systems 10 are frequently employed in cardiac monitoring.

The ECG system 10 may also include a data processing component 20 configured to receive and/or process the electrical signals. For example, the data processing component 20 may convert analog electrical signals to digital data, may analyze the data for recurring events or for events outside of a configured threshold, and/or may process the data for visual display, such as in a waveform, chart, graph, or text presentation. In this manner, the data processing component 20 may produce secondary data, such as timing, rhythm, alert events, variance, averages, and so forth, which may be useful. Similarly, the data processing component 20 may convert the ECG data into formats suitable for storage and/or display.

The processed ECG data may be transmitted to a storage component 22, such as one or more memory chips, magnetic drives, optical drives, and so forth, for short or long-term storage. The storage component 22 may be local or remote from the data processing component 20 and/or data acquisition component 12. For example, the storage component 22 may be a memory or storage device located on a computer network that is in communication with the data processing component 20. In the present context, the storage component 22 may also store programs and routines executed by the data processing component 20, including routines for implementing the present technique.

In addition, the data processing component 20 may transmit the processed ECG data to a printing component 24 for printing as an ECG printout or report. In general, the ECG printout may depict one or more waveforms representing all or part of the processed ECG data. For example, the ECG printout may successively depict only two to three seconds of the ECG data derived from each of the various leads 14 as a respective series of waveforms so that a reviewing doctor may evaluate the overall ECG data set at a glance. In addition, the ECG printout may contain patient and clinical data, such as name, date, procedure, doctor, and so forth, as well as secondary or derived data, such as heart rate and respective intervals for the cardiac phases.

Figure 2:
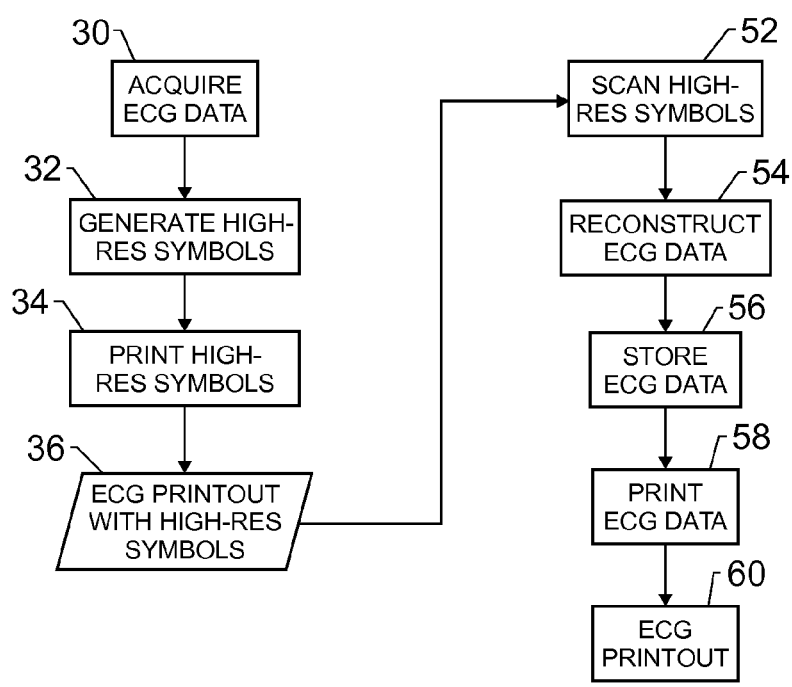
FIG. 2 is a flowchart depicting the technique of generating a set of high-resolution symbols from physiological data and of reconstructing all or part of the physiological data from the set of high-resolution symbols, in accordance with one aspect of the present technique.

The present technique utilizes the aforementioned components of an ECG system 10 in a novel manner to allow the storage and retrieval of the ECG data in a digital form on a printed medium. With reference now to FIG. 2, a flowchart is depicted which further illustrates the present technique. ECG data may be acquired, as depicted at step 30, such as by the data acquisition component 12, leads 14, and contact pads 16 of an ECG system 10.

Figure 3:
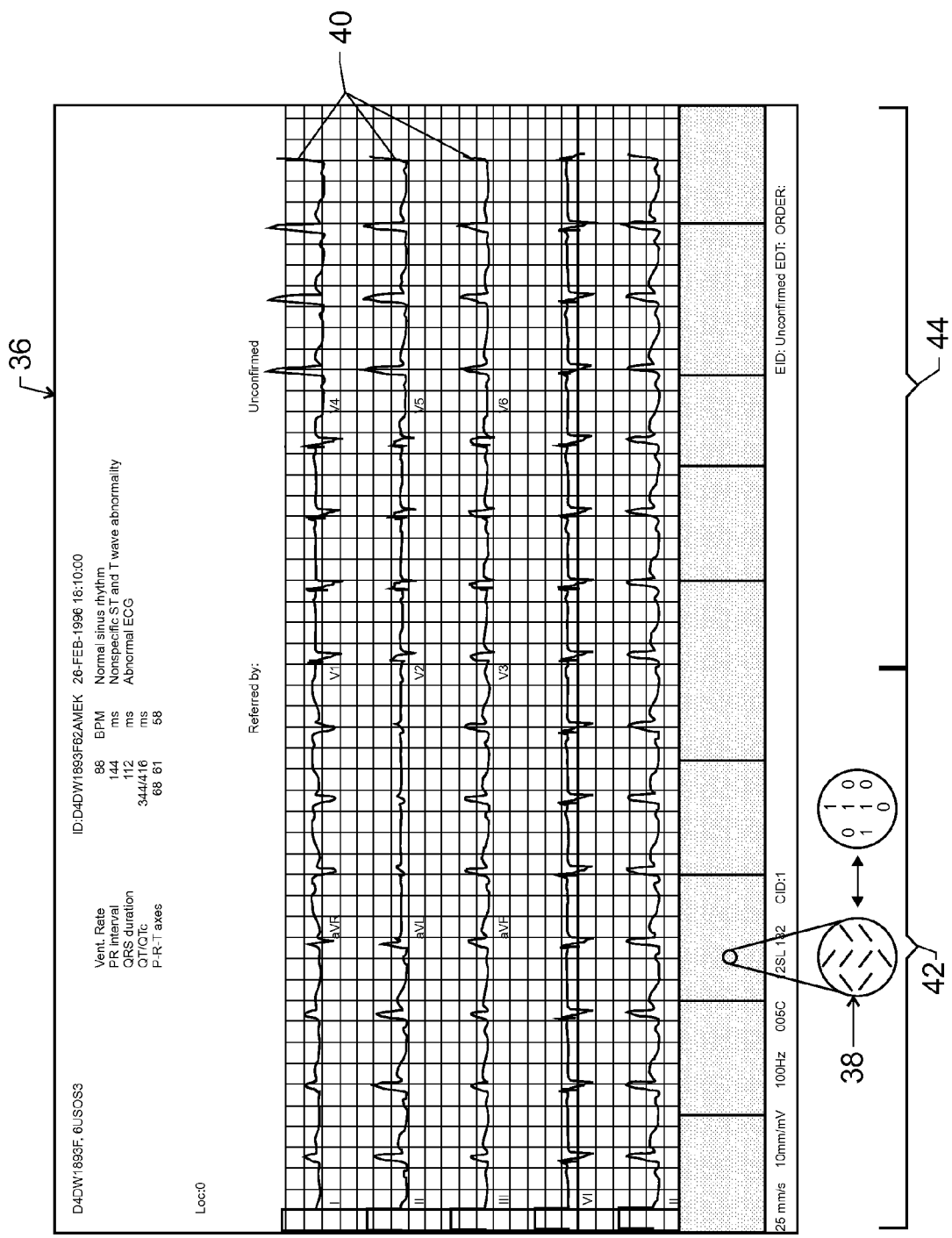
FIG. 3 is an exemplary ECG printout incorporating a set of high-resolution symbols representative of the accompanying digital ECG data, in accordance with one aspect of the present technique.

The acquired ECG data may be used to generate respective high-resolution symbols, as depicted at step 32, which represent the acquired or processed ECG data in a digital, i.e., binary, format. The high-resolution symbols may be printed with the ECG data on an ECG printout 36, as depicted at step 34. An example of such an ECG printout 36 using high-resolution symbols 38 is depicted in FIG. 3. In the depicted ECG printout 36, the high-resolution symbols 38 are printed at high-density along the bottom of the printout 36. Alternatively, the high-resolution symbols 38 may be printed on a separate page of the printout 36, on the back of the printout 36, or on a separate page and/or report.

The high-resolution symbols 38 may consist of various character sets which may be distinguished at high-density and high-resolution (such as 200 dpi, 300 dpi, 400 dpi, 600 dpi, or the like) and which may be used to convey binary information. Various high-density, high-resolution printing and/or two-dimensional barcoding schemes may be employed in selecting a set of high-resolution symbols 38. For instance, appropriate encoding schemes may include Palo Alto Research Center Incorporated's DataGlyph® technology, Cobblestone Software's PaperDisk™ technology, or other encoding techniques known in the art. In addition, factors such as the desired information density, i.e., bytes per square inch of print and/or the desired vertical and horizontal scan and print resolutions, may be considered in selecting a set of high-resolution symbols 38 or a printing scheme.

In the example of FIG. 3, forward slashes (/) and backward slashes (\) are depicted as the high-resolution symbols 38, which respectively equate to 0 and 1, i.e., binary data. The respective ECG waveforms 40 may, therefore, be encoded as binary data in the form of the high-density, high-resolution symbols 38 contained on the printout 36. Similarly, other information that may or may not otherwise appear on the printout, such as patient information, derived parameters, clinic information, procedure information, and so forth, may be encoded by the high-resolution symbols 38.

Furthermore, an increased or reduced amount of ECG data, relative to the ECG waveforms 40 printed on the ECG printout 36, may be encoded via the high-resolution symbols 38. For example, though the printed ECG waveforms 40 may only convey a reduced portion of the total acquired ECG information, such as two to three seconds of information for each lead 14, a larger portion or all of the ECG data may be encoded and printed as high-resolution symbols 38 at high-density. Alternatively, only that ECG data which is present on the printout 36 as a waveform 40 may be encoded on the printout 36 as high-resolution symbols 38. Similarly, less of the ECG data may be encoded than is displayed as waveforms 40. For example, encoding a smaller subset of the ECG data may be desirable when the encoded data is desired primarily as a reference or when ECG data indicative of problems or irregularities is of primary interest.

To provide data integrity, the encoded ECG data may be repeated at regular or irregular intervals to provide the desired degree of data redundancy. Similarly, indicators of data completeness, such as checksum or cyclic redundancy check ("CRC") values, may be included with the encoded ECG data and used to verify the integrity of the data set. For example, referring once again to FIG. 3, a first segment 42 containing the high-resolution symbols 38 may represent a first instance of the encoded data. A second segment 44 may represent a second instance of the encoded data, either in a fully or partially redundant form. In this manner, damage or destruction of a portion of the printout 36 containing the high-resolution symbols 38 will not necessarily result in a non-functional or non-retrievable set of encoded data. As one of ordinary skill in the art will appreciate, the desired degree of redundancy may reflect the importance or irreplaceability of the ECG data, and the second segment 44 may be omitted, leaving that area of the printout blank and/or available for other data, if such redundancy is not desired.

The retrieval or reading of the ECG data encoded by the high-resolution symbols 38 may be accomplished in a variety of manners. For example, if the ECG system 10 includes a scanning component 48 (FIG. 1), the high-resolution symbols 38 may be read by the scanning component 48, as depicted at step 52 of FIG. 2. As will be appreciated, the high-resolution symbols 38 may be scanned directly from the original printout 36 or a copy thereof, allowing for, among other things, electronic transmission of the symbols, such as via e-mail, facsimile, or the like. High-resolution symbols 38 acquired in this manner may be stored temporarily, such as at the storage component 22, or they may be reconstructed by the data processing component 20 to generate the original ECG data encoded by the high-resolution symbols 38, as depicted at step 54 of FIG. 2. Once reconstructed, the ECG data may be stored, such as at the storage component 22, as depicted at step 56 of FIG. 2. The reconstructed ECG data may also be printed by the printing component 24, as depicted at step 58. The printing component 24 may retrieve the ECG data from the data processing component 20 and/or the storage component 22. The resulting second ECG printout 60 may or may not contain high-resolution symbols 38 encoding the ECG data. In addition, the second ECG printout 60 may depict all or a portion of the reconstructed ECG data.

In this manner, the ECG printout 36 commonly used by doctors and other medical personnel may be used to digitally store and reproduce the ECG data. In particular, ECG data obtained by systems that are not connected to a database or storage system may be digitally stored and shared by encoding the ECG data on ECG printouts 36 using the high-resolution symbols 38. In this manner, ECG data obtained during clinical or pharmaceutical trials or at a doctor's office may be digitally stored and subsequently accessed via scanning the high-resolution symbols 38 and reconstructing the ECG data. Furthermore, interpretation and/or reconstruction of the high-resolution symbols 38 would typically be accomplished by a properly configured ECG system 10. As a result, a printout containing ECG data encoded as high-resolution symbols 38 may be publicly accessible or viewable without substantial risk that the encoded patient information would be intelligible to a third party, or even the patient.

Figure 4:
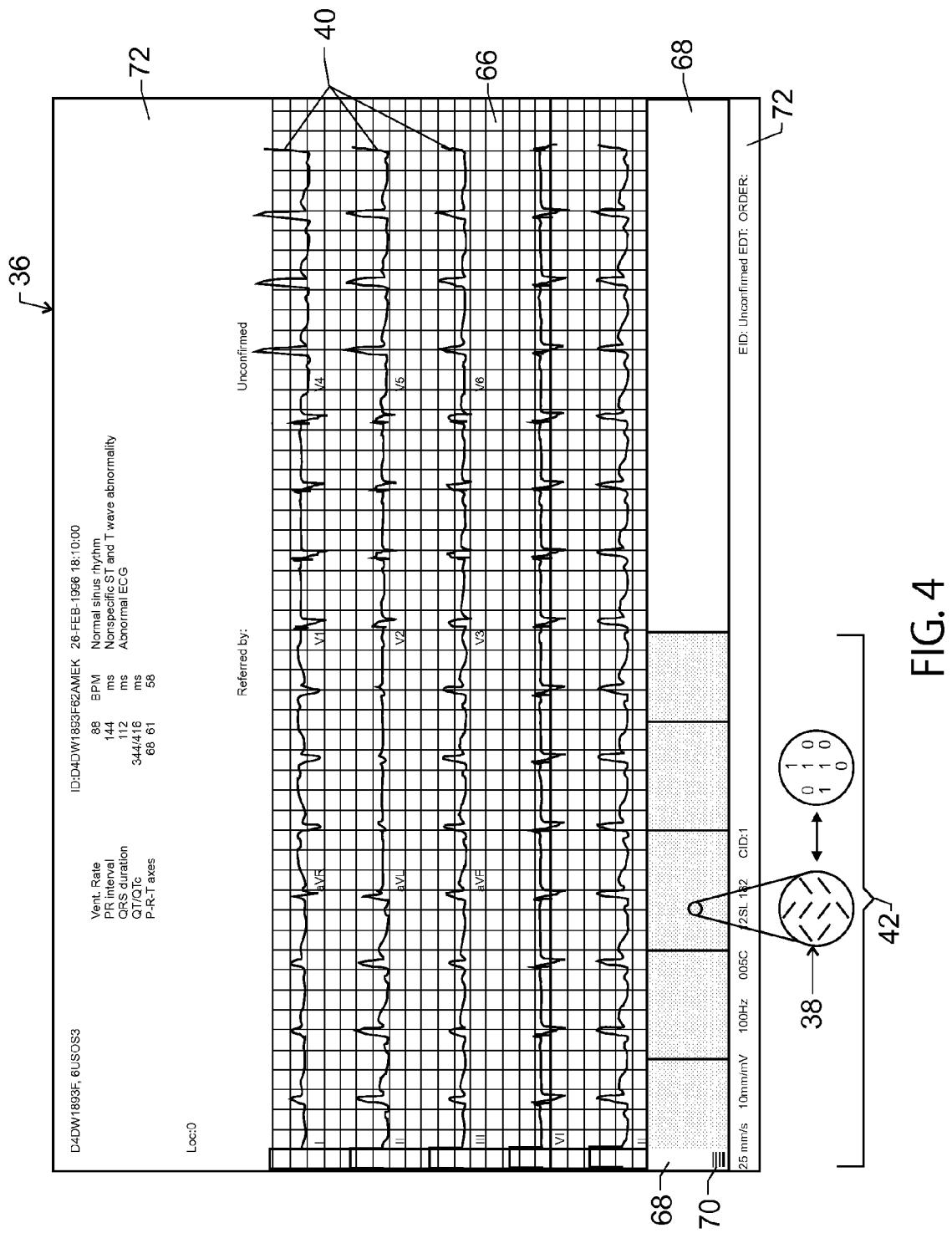
FIG. 4 is an exemplary ECG printout incorporating a plurality of high-resolution symbols representative of the accompanying ECG data and a page registration mark, in accordance with one aspect of the present technique.
Figure 5:
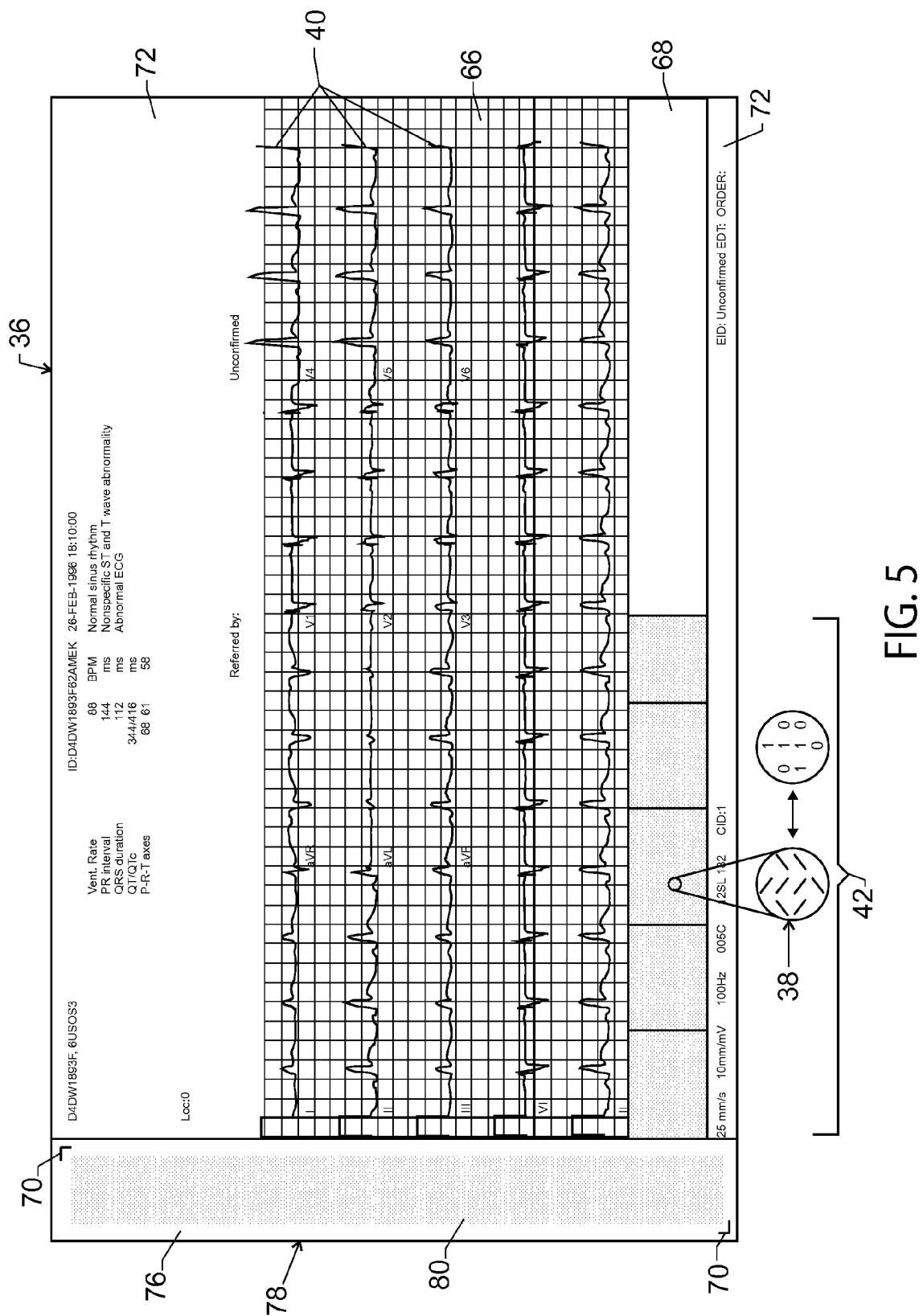
FIG. 5 is an exemplary ECG printout including a region for binary data along a lateral side of the printout, in accordance with one aspect of the present technique.

To facilitate scanning of the high-resolution symbols 38 and reconstruction of physiological data, the data printouts may include one or more page registration marks, as generally illustrated in FIGS. 4-5. For instance, exemplary ECG printouts 36 having such registration marks 70 are illustrated in FIGS. 4-5, in accordance with certain embodiments of the present technique. Similar to the printout of FIG. 3, the exemplary printouts 36 of FIGS. 4-5 each include a first portion or region 66 for receiving the printed ECG waveforms 40 and a second portion or region 68 for receiving the high-resolution symbols 38. As may be appreciated from the discussion above, while only a first data segment 42 corresponding to a first instance of the encoded data is shown printed in the second region 68 (leaving the remaining area of region 68 empty or blank), additional high-resolution symbols 38 may be provided in the remaining space, if desired. As also noted above, such additional high-resolution symbols 38 may encode redundant data, such as segment 44 (FIG. 3), or additional data that is independent of the data encoded in segment 42. In one embodiment, a calculation may be performed by the data processing component 20 (FIG. 1) to determine the amount of space within region 68 that would be filled by a first instance of the encoded data, and the free space that will remain available for printing redundant and/or additional data.

It should be noted that the efficiency of the reconstruction of physiological data from the high-resolution symbols 38 may depend on the rate at which a device, such as the scanning component 48 (FIG. 1), is able to locate the high-resolution symbols 38 on the printout 36. Accordingly, one or more registration marks 70 may be provided on the exemplary printouts 36 to facilitate location and scanning of the encoded data 38 by a scanning device. As will be appreciated, the registration marks 70 may comprise any of a wide array of appropriate shapes and/or forms in full accordance with the present techniques. By way of example, the registration marks 70 of FIG. 4 are a series of horizontal bars of different widths, while those of FIG. 5 are generally L-shaped. It will be recognized, however, that other registration marks may have a different configuration, or may even be omitted, in some embodiments. Also, the printouts 36 may include other regions 72 for receiving and providing additional data, such as a patient identifier, date, procedure, patient statistics, physician, and/or testing parameters, to name but a few.

Although high-resolution symbols 38 are provided within the region 68 along the bottom of the printouts 36 in FIGS. 3-4, it will be appreciated that these symbols may be provided at other locations of the printouts 36 as well. For instance, as illustrated in FIG. 5, a data region 76 may be provided along a lateral side 78 of the printout 36 in addition to, or instead of, region 68. Encoded data 80 may be encoded similarly to the data provided in region 68, i.e., as high-resolution symbols 38, or it may be formatted in some other manner. Further, the encoded data 80 may be redundant of the data provided in region 68, or it may be additional data absent from the region 68. For example, the data encoded within region 68 may be representative of data from a current or recent ECG, while the encoded data 80 of region 76 may represent an earlier ECG or a baseline ECG provided for purposes of comparison. Of course, given sufficient size of the regions, in other embodiments the various encoded data provided in regions 68 and 76 may be provided collectively in either of these two regions, allowing the other region to be omitted from the printout 36. As will also be appreciated, one or more of such regions 68 and/or 76 may be provided at other locations of the printout 36, such as along the upper edge, in accordance with the present technique.

Figure 6:
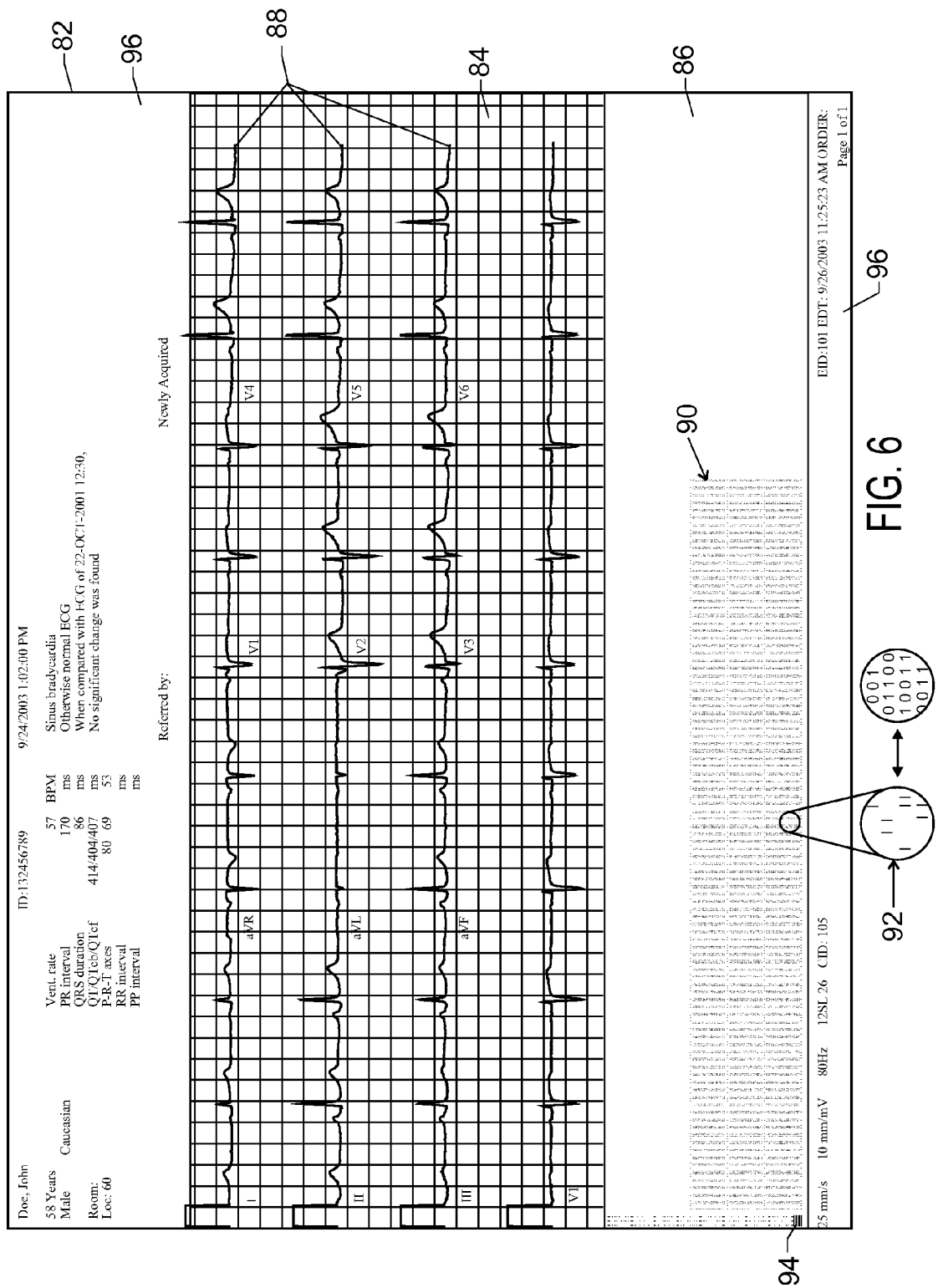
FIG. 6 is an additional exemplary ECG printout in accordance with one aspect of the present technique.

By way of further example, an additional exemplary ECG printout 82 is provided in FIG. 6 in accordance with another embodiment of the present technique. The printout 82 includes a first region 84 for receiving physiological data and a second region 86 for receiving high resolution symbols 38 representative of the physiological data. As generally illustrated above in FIGS. 3-5, the first region 84 may include a background, such as a grid pattern, to facilitate analysis of printed waveforms 88, while the second region 86 is substantially free of such a background or other markings to facilitate printing and scanning of the encoded data or high-resolution symbols 92.

While the encoded data may be provided as a single, unbroken block, the data may instead be broken into various sections, such as rows 90, to facilitate scanning of the data. Additionally, page registration marks 94 may be provided within the region 86. In one embodiment, these registration marks 94 are provided at a location within the region 86 that does not interfere with the printing or scanning of the high-resolution symbols 92. As noted above, the provision of such registration marks 94 may facilitate scanning of the encoded data and reconstruction of physiological data. Also, similar to regions 72 of FIGS. 4-5, additional regions 96 may be provided in the printout 82 for receiving and displaying additional patient data, test data, facility data, and/or the like.

Though the present discussion focuses on an implementation in the field of ECG, other monitoring modalities which typically produce a written document may benefit from the present technique. For example, in the field of medical monitoring, the present technique may be implemented not only in ECG, but also with pulse oximetry, electroencephalography ("EEG"), defibrillation monitors, and so forth. In general, the present technique may be employed with any data, physiological or otherwise, that is customarily printed.

While the inventive arrangements may be susceptible to various modifications and alternative forms, specific embodiments have been shown by way of example in the drawings and have been described in detail herein. However, it should be understood that the inventive arrangements are not intended to be limited to the particular forms disclosed. Rather, the inventive arrangements are to cover all modifications, equivalents, and alternatives falling within the spirit and scope of the inventive arrangements, as defined by the following appended claims.

What is claimed is:

1. A method for storing physiological data, comprising:
   receiving a set of physiological data representative of one or more physiological parameters of interest;
   generating a set of binary symbols from the set of physiological data, wherein generating the set of binary symbols comprises digitally encoding at least a portion of the set of physiological data in a binary format; and
   printing the set of binary symbols to generate a printout including the set of binary symbols, wherein printing the set of binary symbols comprises printing the set of binary symbols on paper including a first portion configured to receive a printed waveform and a second portion configured to receive the set of binary symbols.

2. The method of claim 1, wherein printing the set of binary symbols comprises printing the set of binary symbols on paper having at least one registration mark configured to facilitate scanning of the set of binary symbols from the printout.

3. The method of claim 1, wherein the set of physiological data comprises one or more waveforms.

4. The method of claim 3, wherein the one or more waveforms comprise one or more electrocardiograph ("ECG") waveforms obtained during a first ECG procedure, and further comprising printing an additional set of binary symbols representative of one or more ECG waveforms obtained during a second ECG procedure and/or representative of one or more baseline ECG waveforms.

5. The method of claim 1, comprising printing at least a portion of the set of physiological data on the printout.

6. The method of claim 1, wherein the first portion comprises a grid pattern to facilitate representation of the printed waveform and the second portion comprises a region to facilitate representation of the set of binary symbols.

7. The method of claim 6, comprising scanning the printed set of binary symbols from the second portion and electronically transmitting a copy of the printed set of binary symbols.

8. The method of claim 1, wherein printing the set of binary symbols comprises printing the set of binary symbols on the second portion.

9. The method of claim 8, comprising printing additional binary symbols at least partially redundant of the set of binary symbols.

10. The method of claim 9, wherein printing the set of binary symbols and printing the additional binary symbols comprises substantially filling the area of the second portion with printed binary symbols.

11. A method for acquiring a set of physiological data, comprising:
    receiving a set of binary symbols digitally representative of a set of physiological data, wherein the set of physiological data is representative of at least one physiological parameter of a patient;
    extracting the set of physiological data from the set of binary symbols;
    outputting and/or storing at least a portion of the set of physiological data, and
    printing a set of binary symbols to a print medium;
    wherein receiving the set of binary symbols comprises acquiring the set of binary symbols from the printed medium with a device, and wherein the printed medium comprises a first region including a grid pattern for receiving a waveform and a second region having markings consisting essentially of the set of binary symbols.

12. The method of claim 11, wherein the printed medium includes a page registration mark to facilitate acquisition of the set of binary symbols from the printed medium.

13. The method of claim 11, wherein receiving the set of binary symbols comprises scanning the set of binary symbols from the second region of the printed medium.

14. The method of claim 11, wherein the second region comprises at least one registration mark to facilitate acquisition of the set of binary symbols from the second region.

15. A method, comprising:
  receiving a printout generated via a process comprising:
    receiving a set of physiological data representative of one or more physiological parameters of a patient;
    generating a set of binary symbols from the set of physiological data, wherein generating the set of binary symbols comprises digitally encoding at least a portion of the set of physiological data in a binary format;
    printing the set of binary symbols, wherein printing the set of binary symbols comprises printing the set of binary symbols on paper including a first portion configured to receive a printed waveform and a second portion configured to receive the set of binary symbols;
  printing at least a portion of the set of physiological data; and
  reviewing the printout to evaluate the physiological data of the patient.

16. The method of claim 15, comprising scanning the printed set of binary symbols from a first printout and reconstructing at least a portion of the set of physiological data from the scanned set of binary symbols, wherein printing at least a portion of the set of physiological data comprises printing the reconstructed portion of the set of physiological data onto a second printout.

17. The method of claim 15, wherein the set of physiological data comprises a set of electrocardiograph ("ECG") data.

* * * * *